US012778623B2

(12) United States Patent
Piippo Svendsen et al.

(10) Patent No.: US 12,778,623 B2
(45) Date of Patent: Nov. 3, 2026

(54) ATHERECTOMY DEVICES AND METHODS

(71) Applicant: Cardio Flow, Inc., St. Paul, MN (US)

(72) Inventors: Cassandra Ann Piippo Svendsen, Blaine, MN (US); Charles Anthony Plowe, Blaine, MN (US); Albert Selden Benjamin, St Paul, MN (US); Paul Joseph Robinson, Mahtomedi, MN (US); Evan Leingang, Plymouth, MN (US)

(73) Assignee: Cardio Flow, Inc., St. Paul, MN (US)

( * ) Notice: Subject to any disclaimer, the term of this patent is extended or adjusted under 35 U.S.C. 154(b) by 0 days.

(21) Appl. No.: 19/191,602

(22) Filed: Apr. 28, 2025

(65) Prior Publication Data

US 2025/0261965 A1 Aug. 21, 2025

Related U.S. Application Data

(63) Continuation of application No. 18/816,314, filed on Aug. 27, 2024, now Pat. No. 12,310,617, which is a continuation of application No. 18/440,651, filed on Feb. 13, 2024, now Pat. No. 12,096,956, which is a continuation of application No. 18/386,124, filed on Nov. 1, 2023, now Pat. No. 11,931,065, which is a continuation of application No. 18/231,998, filed on (Continued)

(51) Int. Cl.

| | |
|---|---|
| ***A61B 17/3207*** | (2006.01) |
| *A61B 17/00* | (2006.01) |
| *A61B 17/22* | (2006.01) |
| *A61B 17/32* | (2006.01) |

(52) U.S. Cl.

CPC ................. *A61B 17/320758* (2013.01); *A61B 2017/00057* (2013.01); *A61B 2017/00075* (2013.01); *A61B 2017/00553* (2013.01); *A61B 2017/00557* (2013.01); *A61B 2017/00778* (2013.01); *A61B 2017/22069* (2013.01); *A61B 2017/320004* (2013.01); *A61B 2017/320008* (2013.01); *A61B 2017/320766* (2013.01)

(58) Field of Classification Search

CPC .... A61B 17/320758; A61B 17/320725; A61B 17/3207; A61B 17/320783; A61B 2017/320766; A61B 2017/320775; A61B 2017/32004; A61B 2017/320741; A61B 2017/00778

See application file for complete search history.

(56) References Cited

U.S. PATENT DOCUMENTS

| | | |
|---|---|---|
| 4,784,636 A | 11/1988 | Rydell |
| 4,887,469 A | 12/1989 | Shoptaw |

(Continued)

FOREIGN PATENT DOCUMENTS

| | | |
|---|---|---|
| DE | 3105978 | 12/1981 |
| GB | 2426458 | 5/2005 |

OTHER PUBLICATIONS

"Declaration of Dr. Morten Olgaard Jensen," IPIPR2018-01658, Exhibit 1002, dated Sep. 4, 2018, 93 pages.

(Continued)

*Primary Examiner* — Katherine H Schwiker
(74) *Attorney, Agent, or Firm* — Fish & Richardson P.C.

(57) ABSTRACT

Rotational atherectomy devices and systems can remove or reduce stenotic lesions in blood vessels by rotating an abrasive element within the vessel. The abrasive element can be attached to a distal portion of an elongate flexible drive shaft that extends from a handle assembly.

20 Claims, 8 Drawing Sheets

Related U.S. Application Data

Aug. 9, 2023, now Pat. No. 11,839,400, which is a continuation of application No. 18/132,728, filed on Apr. 10, 2023, now Pat. No. 11,759,229, which is a continuation of application No. 16/827,105, filed on Mar. 23, 2020, now Pat. No. 11,627,983, which is a continuation of application No. 16/198,425, filed on Nov. 21, 2018, now Pat. No. 10,639,064, which is a continuation of application No. 16/197,125, filed on Nov. 20, 2018, now Pat. No. 10,639,063, which is a continuation of application No. 15/091,919, filed on Apr. 6, 2016, now Pat. No. 10,639,062.

(56) References Cited

U.S. PATENT DOCUMENTS

| | | | |
|---|---|---|---|
| 5,019,089 | A | 5/1991 | Farr |
| 5,181,920 | A | 1/1993 | Mueller et al. |
| 5,250,060 | A | 10/1993 | Carbo et al. |
| 5,308,354 | A | 5/1994 | Zacca et al. |
| 5,314,407 | A | 5/1994 | Auth et al. |
| 5,370,653 | A | 12/1994 | Cragg |
| 5,501,694 | A | 3/1996 | Ressemann et al. |
| 5,556,389 | A | 9/1996 | Liprie |
| 5,584,843 | A | 12/1996 | Wulfman et al. |
| 5,667,490 | A | 9/1997 | Keith et al. |
| 5,893,857 | A | 4/1999 | Shturrnan et al. |
| 6,022,363 | A | 2/2000 | Walker |
| 6,024,749 | A | 2/2000 | Shturrnan et al. |
| 6,039,747 | A | 3/2000 | Shturnnan et al. |
| 6,066,152 | A | 5/2000 | Strauss |
| 6,077,282 | A | 6/2000 | Shturrnan et al. |
| 6,132,444 | A | 10/2000 | Shturman et al. |
| 6,494,890 | B1 | 12/2002 | Shturman |
| 6,852,118 | B2 | 2/2005 | Shturrnan et al. |
| 8,177,801 | B2 | 5/2012 | Kallok et al. |
| 8,348,965 | B2 | 1/2013 | Prudnikov |
| 8,353,923 | B2 | 1/2013 | Shturman |
| 8,628,550 | B2 | 1/2014 | Narveson |
| 9,289,230 | B2 | 3/2016 | Cambronne |
| 9,498,600 | B2 | 11/2016 | Rosenthal |
| 9,788,853 | B2 | 10/2017 | Robinson |
| 10,052,122 | B2 | 8/2018 | Higgins et al. |
| 10,052,124 | B2 | 8/2018 | Cambronne |
| 10,064,646 | B2 | 9/2018 | Cambronne |
| 2002/0165567 | A1 | 11/2002 | Shiber |
| 2002/0188276 | A1 | 12/2002 | Evans et al. |
| 2003/0078594 | A1 | 4/2003 | Shturman et al. |
| 2003/0120296 | A1 | 6/2003 | Shturman |
| 2004/0167553 | A1 | 8/2004 | Simpson et al. |
| 2006/0258976 | A1 | 11/2006 | Shturman |
| 2007/0066888 | A1 | 3/2007 | Maschke |
| 2009/0069829 | A1 | 3/2009 | Shturnnan |
| 2009/0182359 | A1 | 7/2009 | Shturnnan |
| 2009/0264908 | A1 | 10/2009 | Kallok |
| 2010/0121361 | A1 | 5/2010 | Plowe et al. |
| 2010/0211088 | A1 | 8/2010 | Narveson |
| 2011/0213391 | A1 | 9/2011 | Rivers |
| 2011/0306995 | A1 | 12/2011 | Moberg |
| 2012/0035633 | A1 | 2/2012 | Shturman et al. |
| 2012/0109170 | A1 | 5/2012 | Shturman et al. |
| 2012/0157906 | A1 | 6/2012 | Underwood et al. |
| 2012/0157907 | A1 | 6/2012 | Underwood et al. |
| 2012/0178986 | A1 | 7/2012 | Campbell et al. |
| 2012/0213391 | A1 | 8/2012 | Usami et al. |
| 2013/0245654 | A1 | 9/2013 | Shturman |
| 2013/0333365 | A1 | 12/2013 | Silet |
| 2014/0081298 | A1 | 3/2014 | Cambronne |
| 2014/0100585 | A1 | 4/2014 | Anderson |
| 2014/0303551 | A1 | 10/2014 | Germain et al. |
| 2015/0080795 | A1 | 3/2015 | Mattison |
| 2015/0094733 | A1 | 4/2015 | Shiber |
| 2015/0164540 | A1 | 6/2015 | Higgins |
| 2016/0157886 | A1 | 6/2016 | Wasdyke |
| 2016/0199093 | A1 | 7/2016 | Cannbronne |
| 2017/0290603 | A1 | 10/2017 | Piippo Svendsen et al. |
| 2018/0235652 | A1 | 8/2018 | Benjamin et al. |
| 2019/0083127 | A1 | 3/2019 | Piippo Svendsen et al. |
| 2019/0090901 | A1 | 3/2019 | Piippo Svendsen et al. |

OTHER PUBLICATIONS

"Declaration of Dr. Morten Olgaard Jensen," IPR2018-01549, Exhibit 1002, dated Aug. 15, 2018, 103 pages.

"Declaration of Kristina Rouw, Ph.D," IPR2018-01549, Exhibit 2001, dated Nov. 29, 2018, 45 pages.

"Declaration of Kristina Rouw, Ph.D," IPR2018-01658, Exhibit 2001, dated Dec. 10, 2018, 44 pages.

"Patent Owner's Preliminary Response," IPR2018-01549, Paper 8, dated Nov. 29, 2018.

"Patent Owner's Preliminary Response," IPR2018-01658, dated, 2018.

"Petition for Inter Partes Review of U.S. Pat. No. 9,788,853 Under 35 U.S.C. § 312 and 37 C.F.R. § 42.104," *Cardiovascular Systems, Inc.* Petitioner v. *Cardio Flow, Inc.* Patent Owner, IPR2018-01549, Paper 1, dated Aug. 17, 2018.

"Petition for Inter Partes Review of U.S. Pat. No. 9,089,362 Under 35 U.S.C. § 312 and 37 C.F.R. § 42.104," *Cardiovascular Systems, Inc.* Petitioner v. *Cardio Flow, Inc.* Patent Owner, IPR2018-01658, Paper 1, dated Sep. 5, 2018.

International Search Report and Written Opinion in International Application No. PCT/US17/26179, dated Oct. 4, 2017, 15 pages.

Invitation to Pay Additional Fees and, Where Applicable, Protest Fee in Application No. PCT/US17/26179, mailed on Jul. 6, 2017, 2 pages.

ATHERECTOMY DEVICES AND METHODS

CLAIM OF PRIORITY

This application is a continuation of U.S. application Ser. No. 18/816,314 filed on Aug. 27, 2024 (now U.S. Pat. No. 12,310,617), which is a continuation of U.S. application Ser. No. 18/440,651 filed on Feb. 13, 2024 (now U.S. Pat. No. 12,096,956), which is a continuation of U.S. application Ser. No. 18/386,124 filed on Nov. 1, 2023 (now U.S. Pat. No. 11,931,065), which is a continuation of U.S. application Ser. No. 18/231,998 filed on Aug. 9, 2023 (now U.S. Pat. No. 11,839,400), which is a continuation of U.S. application Ser. No. 18/132,728 filed on Apr. 10, 2023 (now U.S. Pat. No. 11,759,229), which is a continuation of U.S. application Ser. No. 16/827,105 filed on Mar. 23, 2020 (now U.S. Pat. No. 11,627,983), which is a continuation of U.S. application Ser. No. 16/198,425 filed on Nov. 21, 2018 (now U.S. Pat. No. 10,639,064), which is a continuation of Ser. No. 16/197,125 filed on Nov. 20, 2018 (now U.S. Pat. No. 10,639,063), which is a continuation of U.S. patent application Ser. No. 15/091,919 filed on Apr. 6, 2016 (now U.S. Pat. No. 10,639, 062), the entire contents of which are hereby incorporated by reference.

U.S. Pat. No. 11,627,983), which is a continuation of U.S. application Ser. No. 16/198,425 filed on Nov. 21, 2018 (now U.S. Pat. No. 10,639,064), which is a continuation of Ser. No. 16/197,125 filed on Nov. 20, 2018 (now U.S. Pat. No. 10,639,063), which is a continuation of U.S. patent application Ser. No. 15/091,919 filed on Apr. 6, 2016 (now U.S. Pat. No. 10,639,062), the entire contents of which are hereby incorporated by reference.

TECHNICAL FIELD

This document relates to rotational atherectomy devices and systems for removing or reducing stenotic lesions in blood vessels, for example, by rotating an abrasive element within the vessel to partially or completely remove the stenotic lesion material.

BACKGROUND

Atherosclerosis, the clogging of arteries with plaque, is often a cause of coronary heart disease or vascular problems in other regions of the body. Plaque is made up of fat, cholesterol, calcium, and other substances found in the blood. Over time, the plaque hardens and narrows the arteries. This limits the flow of oxygen-rich blood to organs and other parts of the body.

Blood flow through the peripheral arteries (e.g., carotid, iliac, femoral, renal etc.), can be similarly affected by the development of atherosclerotic blockages. Peripheral artery disease (PAD) can be serious because without adequate blood flow, the kidneys, legs, arms, and feet may suffer irreversible damage. Left untreated, the tissue can die or harbor infection.

One method of removing or reducing such blockages in blood vessels is known as rotational atherectomy. In some implementations, a drive shaft carrying an abrasive burr or other abrasive surface (e.g., formed from diamond grit or diamond particles) rotates at a high speed within the vessel, and the clinician operator slowly advances the atherectomy device distally so that the abrasive burr scrapes against the occluding lesion and disintegrates it, reducing the occlusion and improving the blood flow through the vessel.

SUMMARY

Some embodiments of rotational atherectomy systems described herein can remove or reduce stenotic lesions in blood vessels by rotating an abrasive element to abrade and breakdown the lesion. In some embodiments, the abrasive element is attached to a distal portion of an elongate flexible drive shaft that extends from a handle assembly. In particular embodiments, the handle assembly includes a rotatable turbine member that drives rotation of the drive shaft (for example, in response to pressurized gas or other fluid being controllably delivered to act on the turbine member). In various embodiments, the turbine member is rotatably attached to a carriage that is longitudinally translatable in relation to a housing of the handle assembly (so that the turbine member translates longitudinally with the carriage relative to the housing). Optionally, the handle assembly can include a latch mechanism that can be actuated to allow the carriage to translate to a first position (e.g., a proximal-most position in some embodiments described below) relative to the housing. The first position of the carriage may be a guidewire advancing/withdrawing position in that, while the carriage is in the first position, a guidewire pathway is opened so that a guidewire can be slidably passed through the handle assembly and a lumen of the drive shaft. In some cases, while the carriage is shifted away from the first position (e.g., not in the proximal-most position in some embodiments described below) to an operative position, the guidewire pathway is closed by a seal that hinders liquid egress from a proximal end of the drive shaft.

In one implementation, a rotational atherectomy device includes: an elongate flexible drive shaft comprising a torque-transmitting coil (the drive shaft defining a central lumen and a longitudinal axis); an abrasive element attached to a distal portion of the drive shaft such that a center of mass of the abrasive element is offset from the longitudinal axis; a turbine member coupled to a proximal portion of the drive shaft such that rotation of the turbine member rotates the drive shaft about the longitudinal axis; and an adjustable seal positioned proximally of the turbine member to hinder liquid egress from a proximal end of the central lumen. The adjustable seal has a self-closing portion that is openable to slidably receive a guidewire through the adjustable seal and that is closable to provide a seal of the proximal end of the central lumen.

Such a rotational atherectomy device may optionally include one or more of the following features. The rotational atherectomy device may also include a handle assembly in which the turbine member is housed. The rotational atherectomy device may also include a sheath having a proximal end attached to the handle assembly. The sheath may define a sheath lumen therethrough in which the drive shaft is slidably disposed. In some embodiments, the sheath includes an inflatable member surrounding a distal end portion of the sheath. The inflatable member may define one or more perfusion openings configured to allow fluid flow between a proximal end of the inflatable member and a distal end of the inflatable member. The rotational atherectomy device may also include a carriage to which the turbine member is coupled. In some embodiments, the carriage is longitudinally translatable in relation to a housing of the handle assembly. Such longitudinal translations of the turbine member may result in corresponding longitudinal translations of the drive shaft.

In another implementation, a rotational atherectomy device includes: a handle assembly; an elongate flexible drive shaft comprising a torque-transmitting coil extending from the handle assembly (the drive shaft defining a central lumen and a longitudinal axis); an abrasive element attached to the drive shaft such that a center of mass of the abrasive element is offset from the longitudinal axis; a turbine member disposed within the handle assembly and coupled to the drive shaft such that rotation of the turbine member drives rotation of the drive shaft about the longitudinal axis; and a valve coupled to the handle assembly to control rotation of the turbine member between a rotationally stopped state and a rotationally moving state.

Such a rotational atherectomy device may optionally include one or more of the following features. The rotational atherectomy device may also include a carriage to which the turbine member is rotatably attached. In some embodiments, the carriage may be longitudinally translatable in relation to a housing of the handle assembly. In particular embodiments, the valve may be coupled to the carriage. The valve may be spring biased to a closed configuration resulting in the turbine member being in the rotationally stopped state. In some cases, the valve may be manually actuatable to an open configuration resulting in the turbine member being in the rotationally moving state. The rotational atherectomy device may also include a sheath having a proximal end attached to the handle assembly. Such a sheath may define a sheath lumen therethrough in which the drive shaft is slidably disposed. The sheath may include an inflatable member surrounding a distal end portion of the sheath. In some embodiments, the inflatable member may define one or more perfusion openings configured to allow fluid flow between a proximal end of the inflatable member and a distal end of the inflatable member.

In another implementation, a rotational atherectomy device includes: a handle assembly including a housing; an elongate flexible drive shaft comprising a torque-transmitting coil extending from the housing (the drive shaft defining a central lumen and a longitudinal axis); an abrasive element attached to the drive shaft such that a center of mass of the abrasive element is offset from the longitudinal axis; a turbine member disposed within the housing and coupled to the drive shaft such that rotation of the turbine member rotates the drive shaft about the longitudinal axis; a carriage to which the turbine member is rotatably attached, wherein the carriage is longitudinally translatable in relation to the housing; and a latch mechanism coupled to the housing. Activation of the latch mechanism allows the carriage to translate to a first position in which the handle assembly positions the drive shaft to receive or withdrawn a guidewire.

Such a rotational atherectomy device may optionally include one or more of the following features. When the carriage is located in the first position, an access port defined by the housing may be in fluid communication with the central lumen of the drive shaft. When the carriage is shifted away from the first position, an access port defined by the housing may be disconnected from fluid communication with the central lumen of the drive shaft. The first position may be a proximal-most position of the carriage. When the carriage is located in the proximal-most position and the latch mechanism is deactivated, the carriage may be detained in the proximal-most position. The rotational atherectomy device may also include a valve coupled to the carriage and operable to direct fluid to the turbine member for driving rotation of the turbine member and the drive shaft.

In another implementation, a rotational atherectomy system includes a rotational atherectomy device and a controller operatively connected with the rotational atherectomy device. The rotational atherectomy device includes: a handle assembly including a housing; an elongate flexible drive shaft comprising a torque-transmitting coil extending from the housing (the drive shaft defining a central lumen and a longitudinal axis); an abrasive element attached to the drive shaft such that a center of mass of the abrasive element is offset from the longitudinal axis; a sheath having a proximal end attached to the housing, the sheath defining a longitudinal sheath lumen therethrough in which the drive shaft is slidably disposed; a turbine member disposed within the housing and coupled to the drive shaft such that rotation of the turbine member rotates the drive shaft about the longitudinal axis; an optical sensor configured for detecting rotation of the turbine member; and a carriage to which the turbine member is rotatably attached, wherein the carriage is longitudinally translatable in relation to the housing. The controller is configured for supplying a pressurized gas for rotating the turbine member. In some embodiments, the controller will not supply the pressurized gas unless the optical sensor is in electrical communication with the controller.

Such a rotational atherectomy system may optionally include one or more of the following features. In some embodiments, the controller will not supply the pressurized gas unless a pressure of a flush fluid supplied to the sheath lumen is above a threshold limit value.

In another implementation, a method of performing a rotational atherectomy is provided. The method includes: (i) advancing a drive shaft of a rotation atherectomy device along a guide wire so that an eccentric abrasive element of the drive shaft is directed toward a targeted vessel (the drive shaft comprising torque-transmitting coil extending from a handle assembly and being configured to rotate in response to rotation of a turbine member housed within the handle assembly); (ii) withdrawing the guidewire from a proximal end of the central lumen of the drive shaft and through an adjustable seal positioned proximal of the turbine member (the adjustable seal having a self-closing portion that shifts from an open configuration to a closed configuration that provides a seal); and (iii) after withdrawing the guidewire from the drive shaft and through the adjustable seal, rotating the turbine member coupled to the proximal portion of the drive shaft to drive rotation of the drive shaft about a longitudinal axis of the drive shaft.

In another implementation, another method of performing a rotational atherectomy is provided. The method includes: advancing a drive shaft assembly of a rotation atherectomy device along a guide wire disposed within a vasculature of the patient so that a distal end of the drive shaft assembly is advanced toward the targeted lesion. The drive shaft assembly includes: a sheath comprising an elongate tubular member defining a lumen therethrough and an inflatable member disposed about a distal end portion of the tubular member; a torque-transmitting coil slidably disposed within the lumen and extending distally from a handle assembly (the torque-transmitting coil configured to rotate in response to rotation of a turbine member housed within the handle assembly); and one or more abrasive elements attached to a distal end portion of the torque-transmitting coil. The method also includes: inflating the inflatable member while the inflatable member is positioned at the targeted lesion (wherein the inflating results in compression of the targeted lesion); and rotating the turbine member to drive rotation of the torque-transmitting coil such that the one or more abrasive elements contact the targeted lesion.

Some of the embodiments described herein may provide one or more of the following advantages. First, some embodiments of the rotational atherectomy system are configured to advance the drive shaft and the handle assembly over a guidewire, and to drive the rotation of the drive shaft after the guidewire is withdrawn from the drive shaft (and, optionally, from the handle assembly too). Accordingly, in some embodiments the handle assemblies provided herein include features that allow the drive shaft to be positioned over a guidewire, and that allow the guidewire to be retracted from the drive shaft prior to rotational operations of the drive shaft. In addition, a seal mechanism is provided in particular embodiments that seals the proximal end of the drive shaft lumen after the guidewire has been retracted. Rotational operations of the drive shaft without engagement with a guidewire provides operational advantages such as, but not limited to, providing greater flexibility of the drive shaft, and reducing frictional resistance.

Second, some embodiments of the rotational atherectomy devices and systems provided herein include a handle assembly with a carriage that is manually translatable during rotation of the drive shaft, resulting in longitudinal translation of the rotating abrasive element in relation to a target lesion. In particular embodiments, a valve (or other connector) is mounted on the carriage and operable to control a supply of compressed gas (or other power source) to a carriage-mounted turbine member. The turbine member rotationally drives the drive shaft of the atherectomy device. Hence, in some embodiments the valve for actuating the rotational operation of the drive shaft is conveniently located on the translatable carriage of the handle assembly.

Third, some embodiments of the rotational atherectomy devices and systems include a controller that interfaces with a handle assembly. The controller can be operable, for example, for supplying compressed gas (or other power source) for the turbine member of the handle assembly, and to adjustably control the rotational speed of the turbine member. In some embodiments, the controller can include one or more fail-safe mechanisms that discontinue/prevent the supply of the compressed gas (or other power source) for the turbine member in particular circumstances. For example, in some embodiments the controller will supply the compressed gas to the turbine member (or otherwise drive rotation of the drive shaft) only if a sensor device configured to detect the rotation speed of the turbine member or drive shaft is in electrical communication with the controller. In another example, in various embodiments the controller will supply the compressed gas to the turbine member (or otherwise drive rotation of the drive shaft) only if a detected fluid pressure of a sheath flush fluid (to be delivered into the sheath that carries the drive shaft) is above a threshold limit. Such fail-safe mechanism can, in particular implementations, advantageously maintain safe and effective performance of the rotational atherectomy system.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
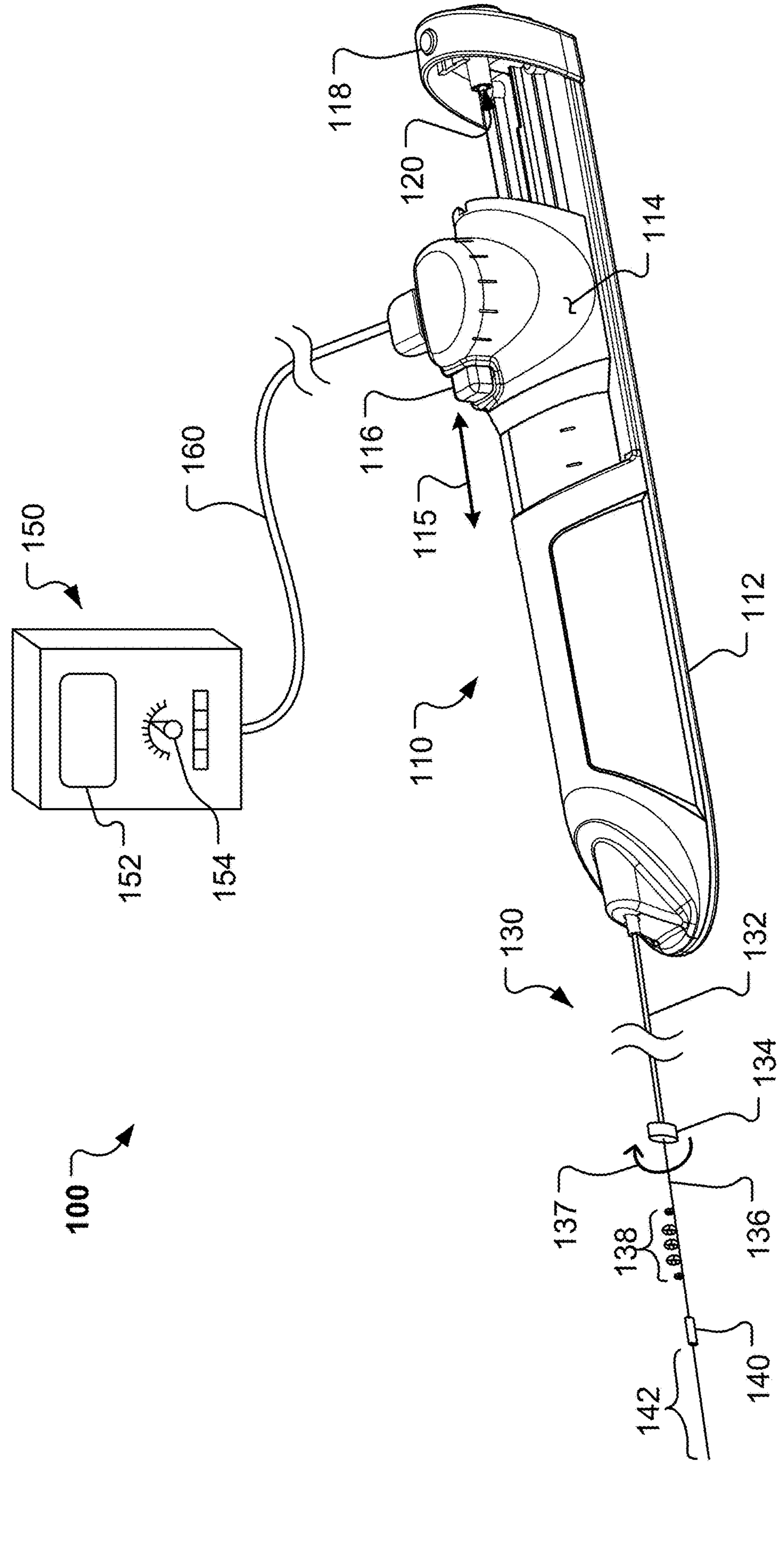
FIG. 1 is a perspective view of an example rotational atherectomy system in accordance with some embodiments.

Referring to FIG. 1, in some embodiments a rotational atherectomy system 100 for removing or reducing stenotic lesions in blood vessels can include an actuator handle assembly 110, an elongate flexible drive shaft assembly 130, and a controller 150. The drive shaft assembly 130 extends distally from the handle assembly 110. The controller 150 is connected to the handle assembly 110 via a cable assembly 160. The handle assembly 110 and controller 150 can be operated by a clinician to control the rotational atherectomy procedure.

In the depicted embodiment, the elongate flexible drive shaft assembly 130 includes a sheath 132 and a flexible drive shaft 136. A proximal end of the sheath 132 is fixed to the handle assembly 110. The flexible drive shaft 136 is slidably and rotatably disposed within a lumen of the sheath 132. Hence, as described further below, during a rotational atherectomy procedure the flexible drive shaft 136 is in motion (e.g., rotating and translating) while the sheath 132 is generally stationary.

In the depicted embodiment, an inflatable member 134 surrounds a distal end portion of the sheath 132. The inflatable member 134 is selectively expandable between a deflated low-profile configuration and an inflated deployed configuration. In some embodiments, the inflatable member 134 can be selectively inflated or deflated by injecting or extracting an inflation fluid (e.g., saline) into the inflatable member 134. Accordingly, in some embodiments the sheath 132 includes an inflation lumen through which the inflation fluid can pass (to and from the inflatable member 134). The inflatable member 134 can be in the deflated low-profile configuration during the navigation of the drive shaft assembly 130 through the patient's vasculature to a target location in a vessel. Then, at the target location, the inflatable member 134 can be inflated so that the outer diameter of the inflatable member 134 contacts the wall of the vessel. In that arrangement, the inflatable member 134 advantageously stabilizes the drive shaft assembly 130 in the vessel during the rotational atherectomy procedure.

In some embodiments, the inflatable member 134 or the sheath 132 may define one or more passageways that facilitate on-going perfusion in the vessel even while the inflatable member 134 is expanded and in contact with the wall of the vessel. Such passageways may be around the perimeter of the inflatable member 134, through the inflatable member 134 in one or more areas within the periphery defined by the inflatable member 134, or through the sheath 132.

The flexible driveshaft 136 is slidably and rotatably disposed within a lumen of the sheath 132. A distal end portion of the driveshaft 136 extends distally of the inflatable member 134 such that the distal end portion of the driveshaft 136 is exposed (i.e., not within the sheath 132). The exposed distal end portion of the driveshaft 136 includes one or more abrasive elements 138, a distal stability element 140, and a distal drive shaft extension portion 142. In the depicted embodiment, the one or more abrasive elements 138 are eccentrically fixed to the driveshaft 136 between the inflatable member 134 and the distal stability element 140. The distal stability element 140 is concentrically fixed to the driveshaft 136 between the one or more abrasive elements 138 and the distal drive shaft extension portion 142. The distal drive shaft extension portion 142 extends distally from the distal stability element 140 and terminates at a free end.

In the depicted embodiment, the distal stability element 140 has a center of mass that is axially aligned with a central longitudinal axis of the drive shaft 136 while the one or more abrasive elements 138 have a center of mass that is axially offset from central longitudinal axis of the drive shaft 136. As the drive shaft 136 is rotated about its longitudinal axis, centrifugal force will cause the one or more abrasive elements 138 to follow a transverse circular orbit around the longitudinal axis. The orbiting one or more abrasive elements 138 will contact the stenotic lesion to ablate the lesion to a reduced size. The distal stability element 140 will remain generally at the longitudinal axis of the drive shaft 136 as the drive shaft 136 is rotated. As described further below, contemporaneous with the rotation of the drive shaft 136, the drive shaft 136 can be translated along the longitudinal axis of the drive shaft 136. Hence, lesions can be ablated radially and longitudinally by virtue of the orbital rotation and translation of the one or more abrasive elements 138, respectively.

The flexible drive shaft 136 of rotational atherectomy system 100 is laterally flexible so that the drive shaft 136 can readily conform to the non-linear vasculature of the patient, and so that a portion of the drive shaft 136 adjacent to the one or more abrasive elements 138 will laterally deflect when acted on by the centrifugal forces resulting from the rotation of the one or more abrasive elements 138. In this embodiment, the drive shaft 136 comprises one or more helically wound wires (or filars). In some embodiments, the one or more helically wound wires are made of a metallic material such as, but not limited to, stainless steel (e.g., 316, 316L, or 316LVM), nitinol, titanium, titanium alloys (e.g., titanium beta 3), carbon steel, or another suitable metal or metal alloy. In some alternative embodiments, the filars are or include graphite, Kevlar, or a polymeric material. In some embodiments, the filars can be woven, rather than wound. In some embodiments, individual filars can comprise multiple strands of material that are twisted, woven, or otherwise coupled together to form a filar. In some embodiments, the filars have different cross-sectional geometries (size or shape) at different portions along the axial length of the drive shaft 136. In some embodiments, the filars have a cross-sectional geometry other than a circle, e.g., an ovular, square, triangular, or another suitable shape.

In this embodiment, the drive shaft 136 has a hollow core. That is, the drive shaft 136 defines a longitudinal lumen running therethrough. The lumen can be used to slidably receive a guidewire therein, as will be described further below. In some embodiments, the lumen can be used to aspirate particulate or to convey fluids that are beneficial for the atherectomy procedure.

In some embodiments, the drive shaft 136 includes a coating on one or more portions of the outer diameter of the drive shaft 136. The coating may also be described as a jacket, a sleeve, a covering, a casing, and the like. In some embodiments, the coating adds column strength to the drive shaft 136 to facilitate a greater ability to push the drive shaft 136 through stenotic lesions. In addition, the coating can enhance the rotational stability of the drive shaft 136 during use. In some embodiments, the coating is a flexible polymer coating that surrounds an outer diameter of at least a portion of drive shaft 136 (e.g., a distal portion of the drive shaft 136 extending from the free end to a location proximal to the inflatable member 134). In some embodiments, a portion of the drive shaft 136 is uncoated (e.g., from the location proximal to the inflatable member 134 to the handle 110). In particular embodiments, the coating is a fluid impermeable material such that the lumen of the drive shaft 136 provides a fluid impermeable flow path along coated portions of the drive shaft 136.

The coating may be made of materials including, but not limited to, PEBEX, PICOFLEX, PTFE, ePTFE, FEP, PEEK, silicone, PVC, urethane, polyethylene, polypropylene, and the like, and combinations thereof. In the some embodiments, the coating covers the distal stability element 140 and the distal extension portion 142, thereby leaving only the one or more abrasive elements 138 exposed (non-coated) along the distal portion of the drive shaft 136. In alternative embodiments, the distal stability element 140 is not covered with the coating, and thus would be exposed like the abrasive element 140. In some embodiments, two or more layers of the coating can be included on portions of the drive shaft 136. Further, in some embodiments different coating materials (e.g., with different durometers and/or stiffnesses) can be used at different locations on the drive shaft 136.

In the depicted embodiment, the distal stability element 140 is a cylindrical member having an inner diameter that surrounds a portion of the outer diameter of the drive shaft 136. In some embodiments, the distal stability element 140 has a longitudinal length that is greater than a maximum exterior diameter of the distal stability element 140. In the depicted embodiment, the distal stability element 140 is coaxial with the longitudinal axis of the drive shaft 136. Therefore, the center of mass of the distal stability element 140 is axially aligned (non-eccentric) with the longitudinal axis of the drive shaft 136. In alternative rotational atherectomy device embodiments, stability element(s) that have centers of mass that are eccentric in relation to the longitudinal axis may be included in addition to, or as an alternative to, the coaxial stability elements 140. For example, in some alternative embodiments, the stability element(s) can have centers of mass that are eccentric in relation to the longitudinal axis and that are offset 180 degrees in relation to the center of mass of the one or more abrasive elements 138.

The distal stability element 140 may be made of a suitable biocompatible material, such as a higher-density biocompatible material. For example, in some embodiments the distal stability element 140 may be made of metallic materials such as stainless steel, tungsten, molybdenum, iridium, cobalt, cadmium, and the like, and alloys thereof. The distal stability element 140 has a fixed outer diameter. That is, the distal stability element 140 is not an expandable member in the depicted embodiment. The distal stability element 140 may be mounted to the filars of the drive shaft 136 using a biocompatible adhesive, by welding, by press fitting, and the like, and by combinations thereof. The coating may also be used to attach or to supplement the attachment of the distal stability element 140 to the filars of the drive shaft 136. Alternatively, the distal stability element 140 can be integrally formed as a unitary structure with the filars of the drive shaft 136 (e.g., using filars of a different size or density, using filars that are double-wound to provide multiple filar layers, or the like). The distal stability element 140 has an exterior cylindrical surface that is smoother and different from an abrasive exterior surface of the one or more abrasive elements 138.

Still referring to FIG. 1, the one or more abrasive elements 138, which may also be referred to as a burr, can comprise a biocompatible material that is coated with an abrasive media such as diamond grit, diamond particles, silicon carbide, and the like. In the depicted embodiment, the one or more abrasive elements 138 includes a total of five discrete abrasive elements that are spaced apart from each other. In some embodiments, one, two, three, four, six, seven, eight, or more than eight discrete abrasive elements are included as the one or more abrasive elements 138. Each of the five discrete abrasive elements can include the abrasive media coating. In the depicted embodiment, the two outermost abrasive elements are smaller in diameter than the three inner abrasive elements.

The center of mass of the one or more abrasive elements 138 is offset from the longitudinal axis of the drive shaft 136. Therefore, as the eccentric one or more abrasive elements 138 are rotated in an orbital path, at least a portion of the abrasive surface of the one or more abrasive elements 138 can make contact with surrounding stenotic lesion material. As with the distal stability element 140, the eccentric one or more abrasive elements 138 may be mounted to the filars of the drive shaft 136 using a biocompatible adhesive, welding, press fitting, and the like. Alternatively, the one or more abrasive elements 138 can be integrally formed as a unitary structure with the filars of the drive shaft 136 (e.g., using filars that are wound in a different pattern to create an axially offset structure, or the like).

In some embodiments, the spacing of the distal stability element 140 relative to the one or more abrasive elements 138 and the length of the distal extension portion 142 can be selected to advantageously provide a stable and predictable rotary motion profile during high-speed rotation of the drive shaft 136. For example, in embodiments that include the distal driveshaft extension portion 142, the ratio of the length of the distal driveshaft extension 142 to the distance between the centers of the one or more abrasive elements 138 and the distal stability element 140 is about 1:1, about 1.1:1, about 1.2:1, about 1.5:1, about 2:1, about 2.5:1, about 3:1, or higher than 3:1.

Still referring to FIG. 1, the rotational atherectomy system 100 also includes the actuator handle assembly 110. The actuator handle assembly 110 includes a housing 112 and a carriage assembly 114. The carriage assembly 114 is slidably translatable along the longitudinal axis of the handle assembly 110 as indicated by the arrow 115. As the carriage assembly 114 is translated in relation to the housing 112, the drive shaft 136 translates in relation to the sheath 132 in a corresponding manner.

The carriage assembly 114 includes a valve actuator 116. In the depicted embodiment, the valve actuator 116 is a button that can be depressed to actuate a compressed gas control valve (FIGS. 9 and 10) mounted to the carriage assembly 114. While the valve actuator 116 is depressed, a compressed gas (e.g., air, nitrogen, etc.) is supplied through the valve to a turbine member (FIG. 10) that is rotatably coupled to the carriage assembly 114 and fixedly coupled to the drive shaft 136. Hence, an activation of the valve actuator 116 will result in a rotation of the turbine member and, in turn, the drive shaft 136 (as depicted by arrow 137). It should be understood that the rotational atherectomy system 100 is configured to rotate the drive shaft 136 at a high speed of rotation (e.g., 20,000-160,000 rpm) such that the eccentric one or more abrasive elements 138 revolve in an orbital path to thereby contact and remove portions of a target lesion (even those portions of the lesion that are spaced farther from the axis of the drive shaft 136 than the maximum radius of the one or more abrasive elements 138).

To operate the handle assembly 110 during a rotational atherectomy procedure, a clinician can grasp the carriage assembly 114 and depress the valve actuator 116 with the same hand. The clinician can move (translate) the carriage assembly 114 distally and proximally by hand (in relation to the housing 112), while maintaining the valve actuator 116 in the depressed state. In that manner, a target lesion(s) can be ablated radially and longitudinally by virtue of the resulting orbital rotation and translation of the one or more abrasive elements 138, respectively.

In the depicted embodiment, the handle assembly 110 also includes a carriage docking latch actuator 118. As described further below, the carriage docking latch actuator 118 can be actuated (e.g., depressed) to allow the carriage assembly 114 to translate to a proximal-most position in which an access port 120 defined by the housing 112 is put into fluid communication with the lumen of the drive shaft 136. In that proximal-most position, a guidewire can be readily installed or removed from the lumen of the drive shaft 136 via the access port 120. While the carriage assembly 114 is in the proximal-most position, the carriage docking latch actuator 118 can be released and the carriage assembly 114 will remain releasably latched in the proximal-most position. Thereafter, actuation of the carriage docking latch actuator 118 will allow the carriage assembly 114 to be translated distally away from the proximal-most position. While the carriage assembly 114 is located in any position other than the proximal-most position, the carriage docking latch actuator 118 will not allow the carriage assembly 114 to be moved into the proximal-most position unless the carriage docking latch actuator 118 is actuated.

Still referring to FIG. 1, the rotational atherectomy system 100 also includes the controller 150. In some embodiments, the controller 150 is pole-mounted. The controller 150 can be used to control particular operations of the handle assembly 110 and the drive shaft assembly 130. For example, the controller 150 can be used to compute, display, and adjust the rotational speed of the drive shaft 136.

In some embodiments, the controller 150 can include electronic controls that are in electrical communication with a turbine RPM sensor located on the carriage assembly 114. The controller 150 can convert the signal(s) from the sensor into a corresponding RPM quantity and display the RPM on a user interface 152. If a speed adjustment is desired, the clinician can increase or decrease the rotational speed of the drive shaft 136 using an RPM adjustment device 154 on the controller 150. In result, a flow or pressure of compressed gas supplied from the controller 150 to the handle assembly 110 (via the cable assembly 160) will be modulated. The modulation of the flow or pressure of the compressed gas will result in a corresponding modulation of the RPM of the turbine member and the drive shaft 136.

In some embodiments, the controller 150 includes one or more interlock features that can enhance the functionality of the rotational atherectomy system 100. In one such example, if the controller 150 does not detect any electrical signal (or a proper signal) from the turbine RPM sensor, the controller 150 can discontinue the supply of compressed gas. In another example, if a pressure of a flush liquid supplied to the sheath 132 is below a threshold pressure value, the controller 150 can discontinue the supply of compressed gas.

Figure 2:
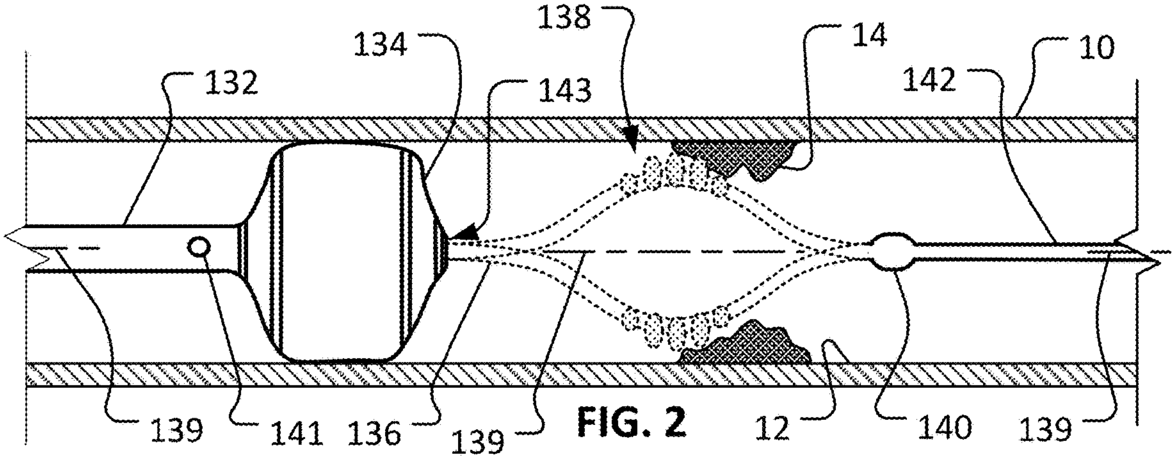
FIG. 2 shows an example rotational atherectomy device in use within a target vessel that includes a lesion. An abrasive element of the rotational atherectomy device is being rotated at a first longitudinal position.
Figure 3:
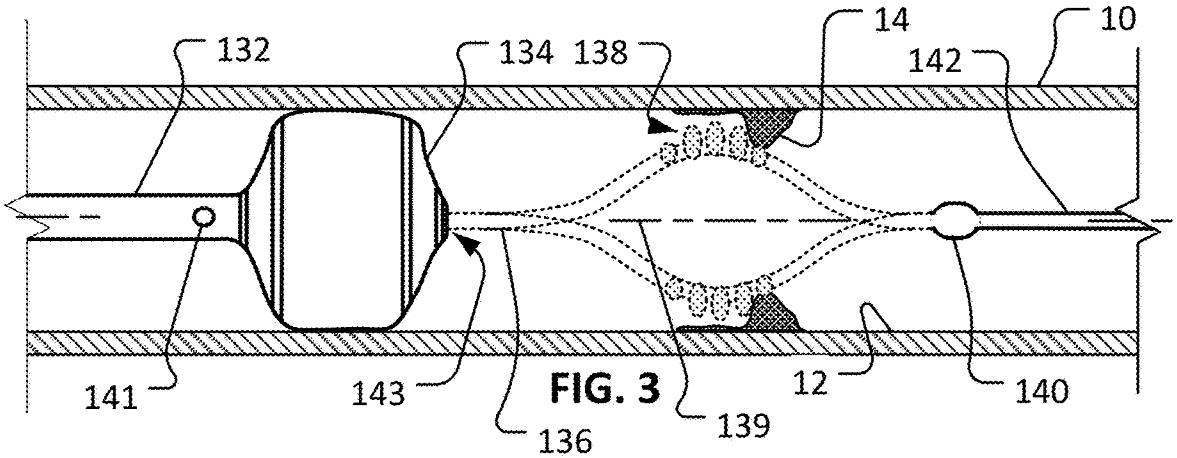
FIG. 3 shows the rotational atherectomy device of FIG. 2 with the abrasive element being rotated at a second longitudinal position that is distal of the first longitudinal position.
Figure 4:
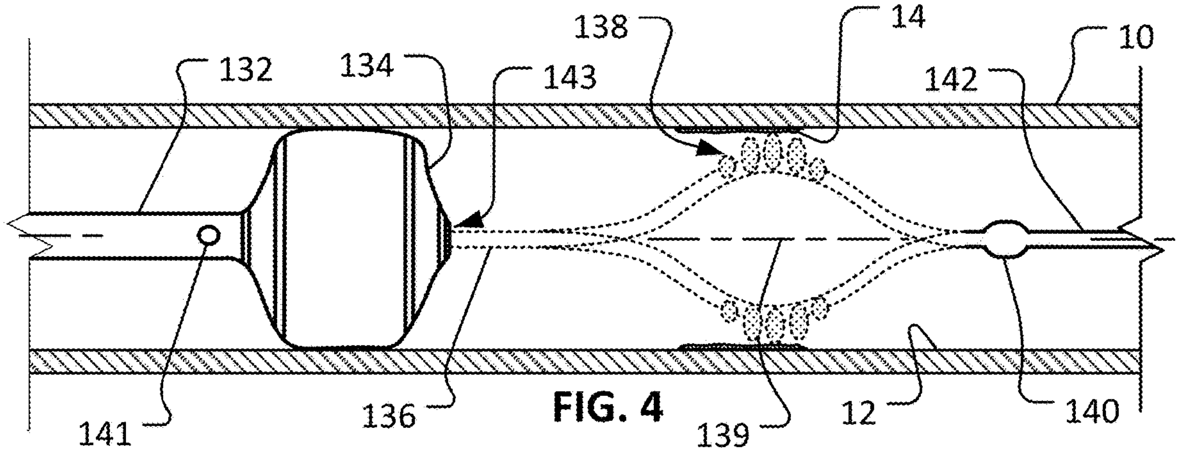
FIG. 4 shows the rotational atherectomy device of FIG. 2 with the abrasive element being rotated at a third longitudinal position that is distal of the second longitudinal position.

Referring also to FIGS. 2-4, the rotational atherectomy system 100 can be used to treat a vessel 10 having a stenotic lesion 14 along an inner wall 12 of the vessel 10. The rotational atherectomy system 100 is used to fully or partially remove the stenotic lesion 14, thereby removing or reducing the blockage within the vessel 10 caused by the stenotic lesion 14. By performing such a treatment, the blood flow through the vessel 10 may be thereafter increased or otherwise improved. The vessel 10 and lesion 14 are shown in longitudinal cross-sectional views to enable visualization of the rotational atherectomy system 100.

Briefly, in some implementations the following activities may occur to achieve the deployed arrangement shown in FIGS. 2-4. An introducer sheath (not shown) can be percutaneously advanced into the vasculature of the patient. A guidewire (not shown) can then be inserted through a lumen of the introducer sheath and navigated within the patient's vasculature to a target location (e.g., the location of the lesion 14). Techniques such as x-ray fluoroscopy or ultrasonic imaging may be used to provide visualization of the guidewire and other atherectomy system components during placement. Next, the rotational atherectomy system 100 can be inserted over the guidewire. For example, an opening to the lumen of the drive shaft 136 at the distal free end of the drive shaft 136 can be placed onto the guidewire, and then the drive shaft assembly 130 and handle assembly 110 can be gradually advanced over the guidewire to the position in relation to the lesion 14 as shown. The inflatable member 134 is configured in its deflated, low-profiled configuration during the advancing. In some cases, the drive shaft 136 is disposed fully within the lumen of the sheath 132 during the advancing. In some cases, a distal end portion of the drive shaft 136 extends from the distal end opening 143 of the sheath 132 during the advancing. Preferably, the carriage assembly 114 is latched in its proximal-most docking position during the advancement of the drive shaft assembly 130, and handle assembly 110 over the guidewire. Eventually, after enough advancing, the proximal end of the guidewire will extend proximally from the handle assembly 110 (via the access port 120 defined by the handle housing 112). Next, the guidewire can be withdrawn from the patient by pulling the guidewire out from the access port 120 defined by the handle housing 112. After withdrawing the guidewire, the carriage docking latch actuator 118 can be activated to allow the carriage assembly 114 to move from its proximal-most position. The inflatable member 134 can be inflated so that it contacts the inner wall 12 of the vessel 10. Then, the rotation and translational motions of the drive shaft 136 and one or more abrasive elements 138 (as depicted by FIGS. 2-4) can be commenced to perform ablation of the lesion 14.

In some implementations, prior to the ablation of the lesion 14 by the one or more abrasive elements 138, the inflatable member 134 can be used as an angioplasty balloon. That is, sheath 132 can be advanced to a position that places the inflatable member 134 within the lesion 14. The inflatable member 134 can then be inflated to compress the lesion 14 against the inner wall 12 of the vessel 10. Thereafter, the rotational atherectomy procedure can be performed. In some implementations, the inflatable member 134 can be used as an angioplasty balloon after the rotational atherectomy procedure is performed. In some implementations, additionally or alternatively, a stent can be placed at lesion 14 using the inflatable member 134 or another balloon member associated with the drive shaft assembly 130 after the rotational atherectomy procedure is performed.

In some implementations, the guidewire is withdrawn completely out of the lumen of the drive shaft 136 prior to ablation of the lesion 14 (as described above). In other implementations, the guidewire is withdrawn only partially. That is, in some implementations a portion of the guidewire remains within the lumen of the drive shaft 136 during rotation of the drive shaft 136, but remains only in the portion that is not subject to the significant orbital path in the area of the one or more abrasive elements 138. After the guidewire is withdraw (fully or partially), the drive shaft 136 is then rotated at a high rate of rotation (e.g., 20,000-160,000 rpm) such that the eccentric one or more abrasive elements 138 revolve in an orbital path about an axis of rotation and thereby contacts and removes portions of the lesion 14.

Still referring to FIGS. 2-4, the rotational atherectomy system 100 is depicted during the high-speed rotation of the drive shaft 136. The centrifugal force acting on the eccentrically weighted one or more abrasive elements 138 causes the one or more abrasive elements 138 to orbit in an orbital path around the axis of rotation 139. In some implementations, the orbital path can be somewhat similar to the motion of a "jump rope." As shown, some portions of the drive shaft 136 (e.g., a portion that is just distal of the inflatable member 134 and another portion that is distal of the distal stability element 140) can remain in general alignment with the axis of rotation 139, but the particular portion of the drive shaft 136 adjacent to the one or more abrasive elements 138 is not aligned with the axis of rotation 139 (and instead orbits around the axis 139).

In some implementations, as the one or more abrasive elements 138 rotates, the clinician operator slowly advances the carriage assembly 114 distally (and, optionally, reciprocates both distally and proximally) along the longitudinal axis of the drive shaft 136 and the handle assembly 110 so that the abrasive surface of the one or more abrasive elements 138 scrapes against additional portions of the occluding lesion 14 to reduce the size of the occlusion, and to thereby improve the blood flow through the vessel 10. This combination of rotational and translational motion of the one or more abrasive elements 138 is depicted by the sequence of FIGS. 2-4.

In some embodiments, the inflatable member 134 or the sheath 132 may define one or more passageways 141 that facilitate on-going perfusion in the vessel even while the inflatable member 134 is expanded and in contact with the wall of the vessel. Such passageways 141 may be around the perimeter of the inflatable member 134 (between the inflatable member 134 and the inner wall 12 of the vessel 10), through the inflatable member 134 in one or more areas within the periphery defined by the inflatable member 134, or through the sheath 132 (as depicted). In the depicted arrangement, blood in the vessel 10 can continue to flow by passing through the sheath 132 between the one or more passageways 141 and the distal end opening 143 of the sheath 132.

Figure 5:
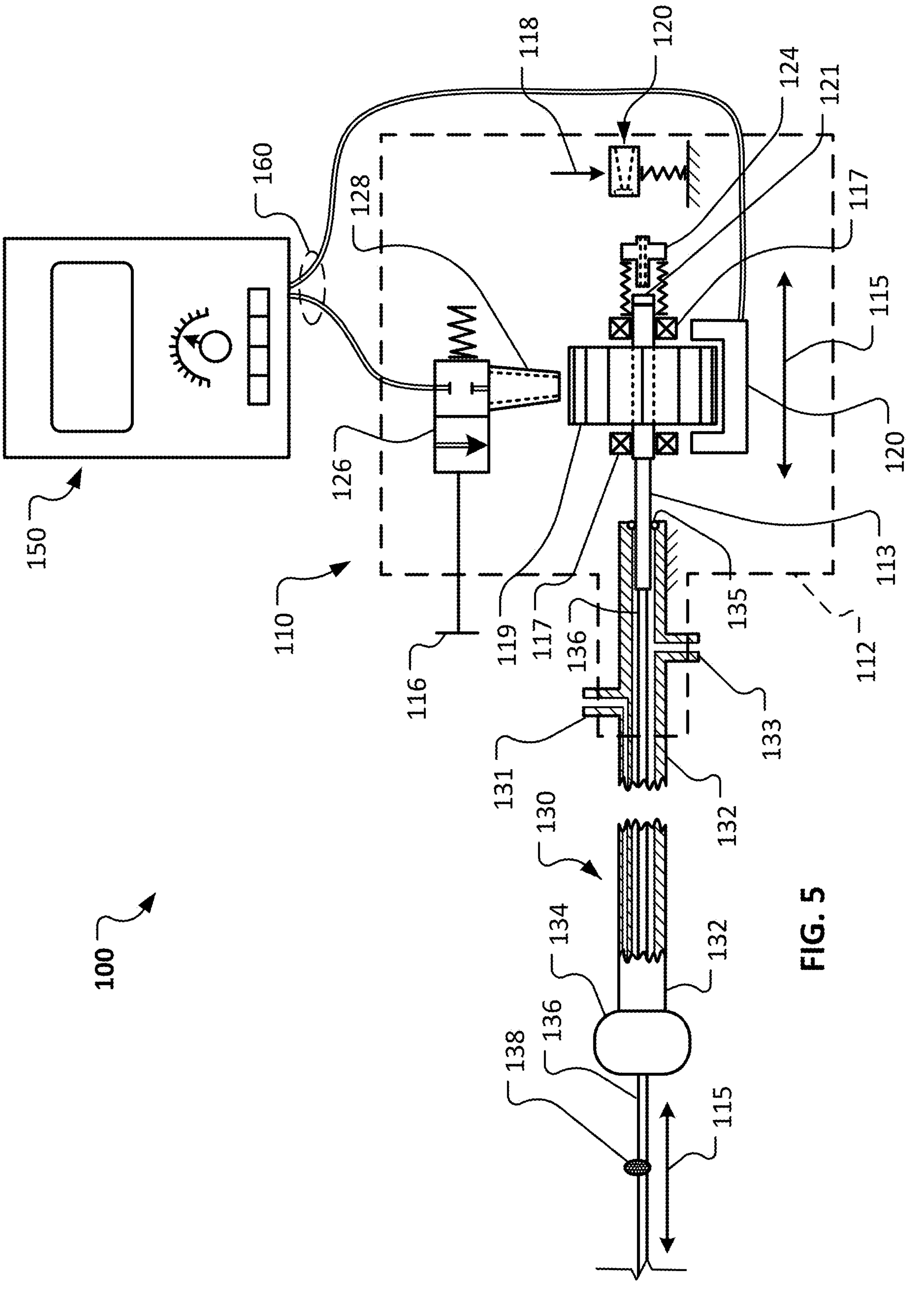
FIG. 5 is a schematic diagram of an example rotational atherectomy system including a drive shaft with an abrasive element, a handle assembly, and a controller.

Referring to FIG. 5, the rotational atherectomy system 100 can be depicted schematically to allow for further description of the system 100. Here, the sheath 132 is shown in partial longitudinal cross-section to allow for visualization of the features therein, and the boundary of the handle assembly 110 is shown in dashed lines. As described above, the rotational atherectomy system 100 includes the handle assembly 110, the drive shaft assembly 130, and the controller 150.

The drive shaft assembly 130 includes the sheath 132 (with the inflatable member 136) and the drive shaft 136. The drive shaft 136 is slidably and rotatably disposed within a longitudinal lumen defined by the sheath 132. A clearance exists between the drive shaft 136 and the inner diameter of the longitudinal lumen defined by the sheath 132. A flush fluid can be supplied via a flush fluid port 133 into the clearance between the drive shaft 136 and the inner diameter of the longitudinal lumen defined by the sheath 132. The flush fluid can provide lubrication and cooling between the drive shaft 136 and the inner diameter of the longitudinal lumen defined by the sheath 132. Additionally, the flush fluid can inhibit blood ingress into the drive shaft assembly 130. In some embodiments, the flush fluid port 133 can be used for aspiration.

The drive shaft assembly 130 also includes an inflation fluid port 131. The inflation fluid port 131 is in fluid communication with a lumen defined within the wall of the sheath 132 and with the inflatable member 134. Hence, by supplying a fluid via the inflation fluid port 131 (e.g., using a syringe, pump, etc.) the inflatable member 134 can be inflated to its expanded configuration. Conversely, by withdrawing a fluid via the inflation fluid port 131, the inflatable member 134 can be deflated to its collapsed, low-profile configuration.

The proximal end of the sheath 132 is fixed to the housing 112 of the handle assembly 110. In some embodiments, pig tails are coupled to the inflation fluid port 131 and or the flush fluid port 133.

The handle assembly 110 includes the turbine member 119. The turbine member 119 can be driven by compressed gas supplied through a valve 126 and a nozzle 128. The turbine member 119, valve 126, and nozzle 128 are mounted to the carriage assembly 114 (FIG. 1). The turbine member 119 rotates on bearings 117.

In the depicted configuration, the valve 126 is closed. Therefore, the turbine member 119 and the drive shaft 136 are not rotating in the depicted configuration.

The handle assembly 110 also includes an RPM sensor 120. In some embodiments, the RPM sensor 120 is an optical sensor that detects the passage of each vane of the turbine member 119 as the turbine member 119 is rotating.

In the depicted embodiment, a proximal end portion of the drive shaft 136 is coupled with the turbine member 119 using an intermediary tubular member 113. The tubular member 113 can be a stainless steel tube, for example. In some embodiments, the proximal end portion of the drive shaft 136 is bonded within a lumen of the intermediary tubular member 113 using an adhesive (e.g., a cyanoacrylate type of adhesive, and the like). A seal 135 exists between the outer diameter of the intermediary tubular member 113 and the inner diameter of the proximal end of the sheath 132. The seal 135 inhibits the egress of the flush fluid supplied via the flush fluid port 133.

The arrangement of the proximal end portion of the drive shaft 136, the intermediary tubular member 113, and the turbine member 119 is such that an opening to the lumen of the drive shaft 136 is located proximal of the turbine member 119. An adjustable seal 121 is positioned at the location of the opening. The adjustable seal 121 includes a self-closing portion. While the self-closing portion is closed, the adjustable seal 121 hinders liquid egress from the proximal end of the lumen defined by the drive shaft 136 (and the lumens defined by the intermediary tubular member 113 and the turbine member 119). While the self-closing portion is opened, a guidewire can be slidably received through the adjustable seal 121, and into the lumens defined by the proximal end portion of the drive shaft 136, the intermediary tubular member 113, and the turbine member 119. The operations of the adjustable seal will be described further below (in reference to FIG. 8).

Figure 6:
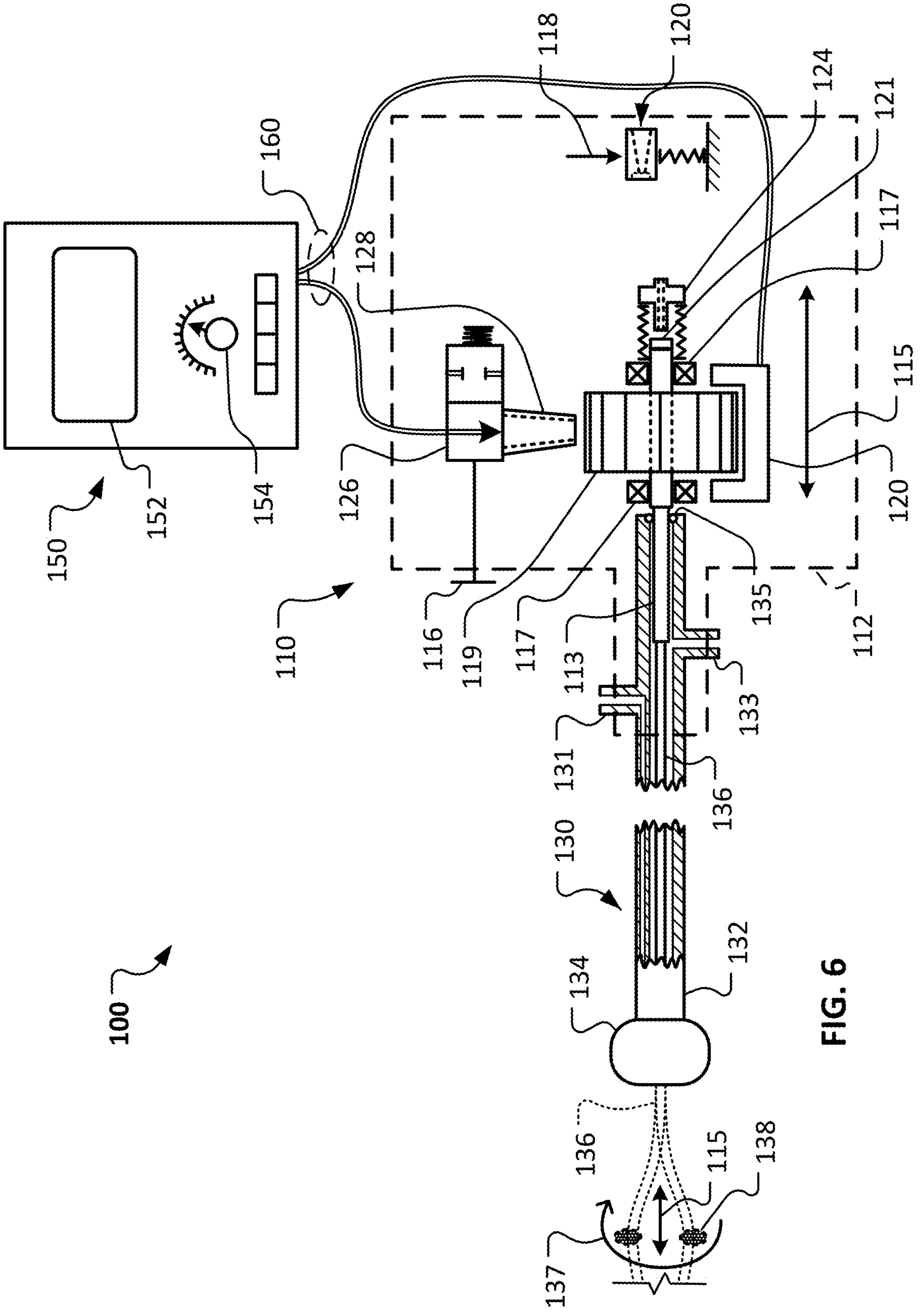
FIG. 6 shows the schematic diagram of FIG. 5 with a carriage of the handle assembly and the abrasive element in distal-most positions.

Referring to FIG. 6, the valve 126 can be opened by actuation of the valve actuator 116, resulting in flow of compressed gas from the controller 150, through the valve 126 and the nozzle 128, and rotation of the turbine member 119. The rotation of the turbine member 119, in turn, results in a rotation of the drive shaft 136 as depicted by arrow 137. The clinician operator can view the measured RPM of the turbine/drive shaft via the user interface 152, and adjust the speed of the rotation via the RPM adjustment device 154 on the controller 150.

Additionally, the clinician operator can translate the carriage assembly 114 (FIG. 1) and the drive shaft 136 as depicted by arrow 115. In the depicted arrangement, the carriage assembly 114 has been translated to a distal-most position.

Figure 7:
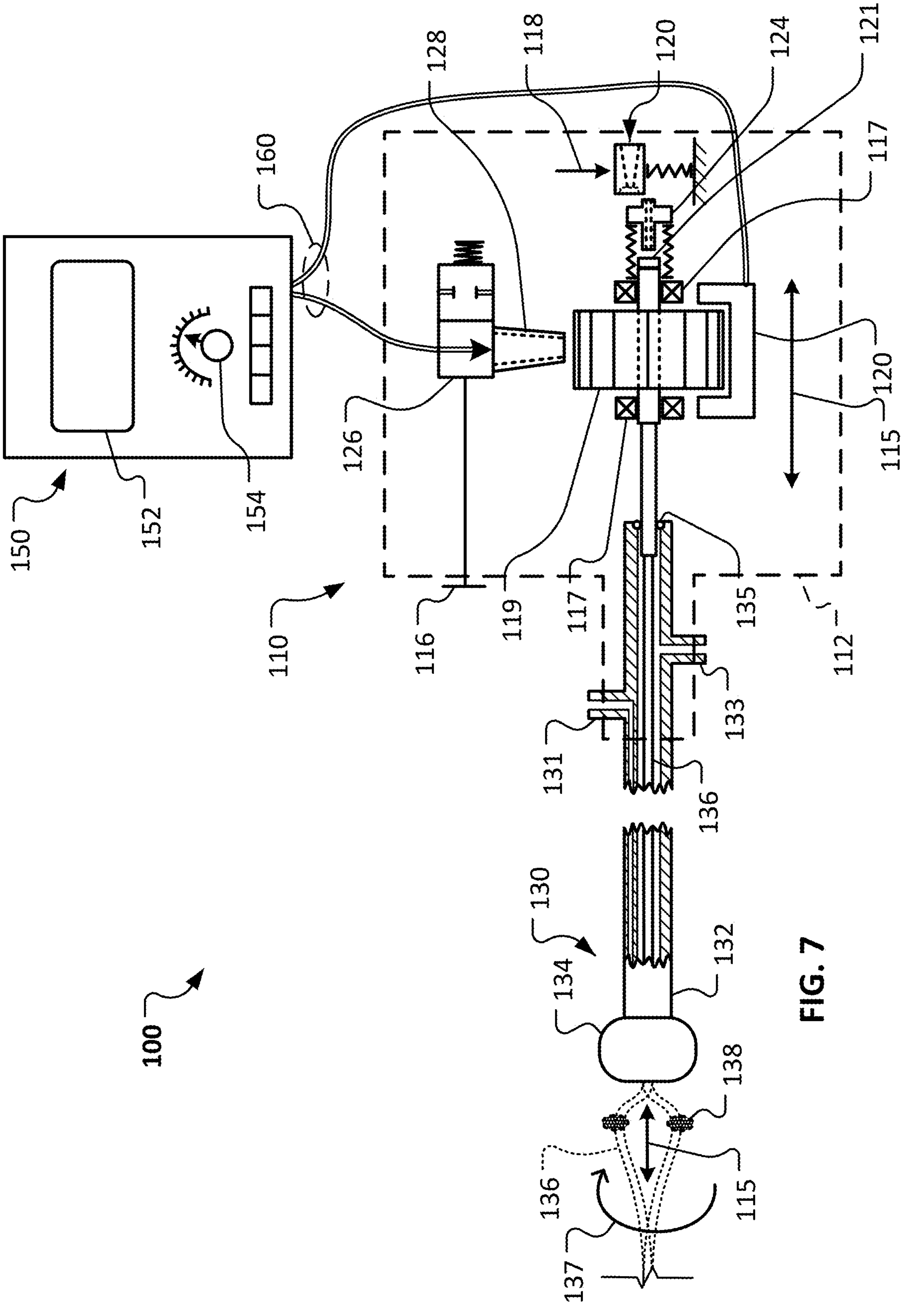
FIG. 7 shows the schematic diagram of FIG. 5 with the carriage of the handle assembly and the abrasive element in positions that are proximal of the positions shown in FIG. 6.

Referring also to FIG. 7, the clinician operator can also translate the carriage assembly 114 (FIG. 1) and the drive shaft 136 (as depicted by arrow 115) to a proximal position. In some cases, the clinician operator may oscillate the carriage assembly 114 between the distal position of FIG. 6 and the proximal position of FIG. 7 (or to one or more intermediate positions therebetween) multiple times while the drive shaft 136 is rotating so as to ablate a lesion.

Figure 8:
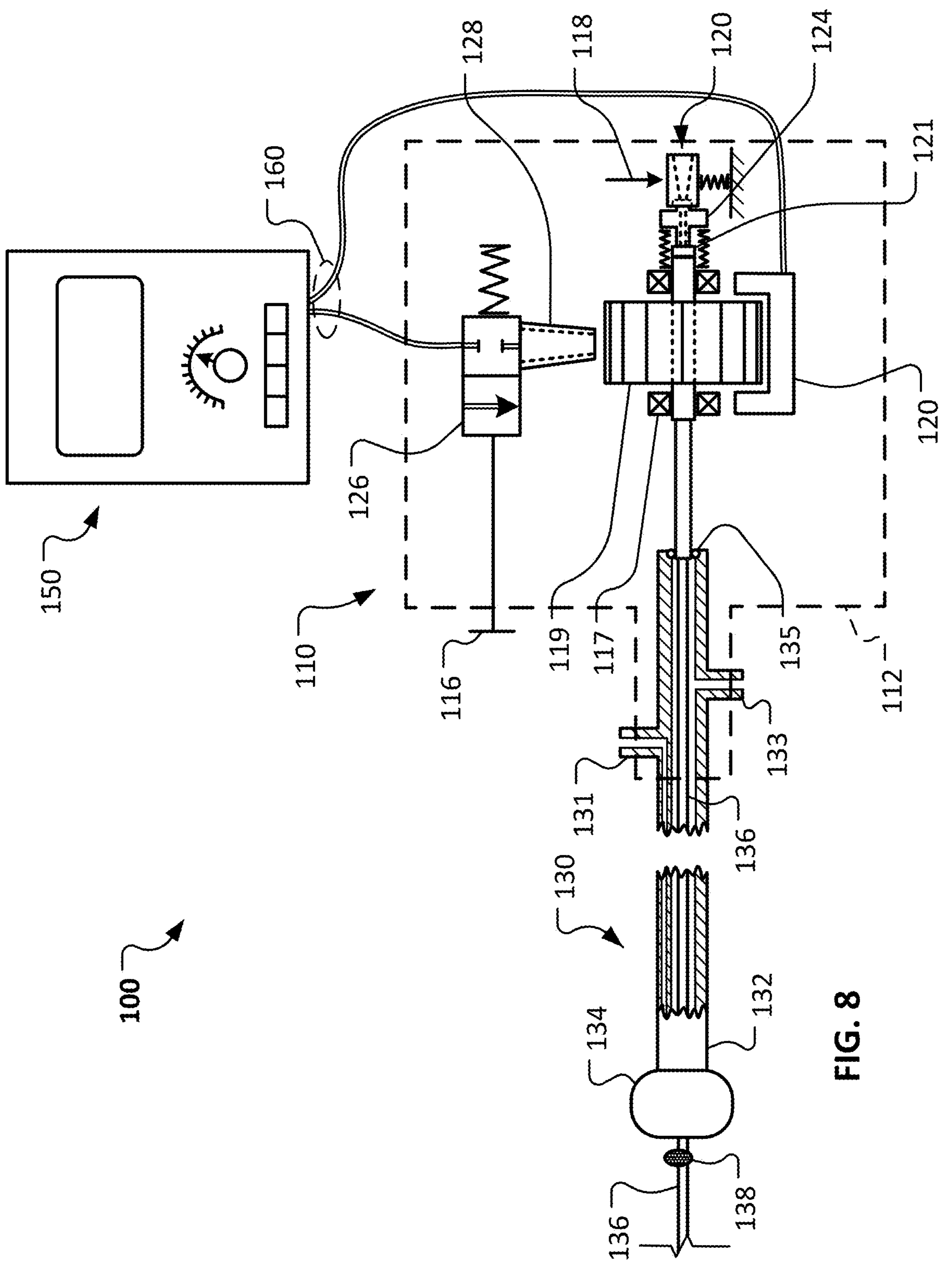
FIG. 8 shows the schematic diagram of FIG. 5 with the carriage of the handle assembly and the abrasive element in proximal-most positions.

Referring to FIG. 8, the carriage assembly 114 (FIG. 1) can also be translated to a proximal-most position as illustrated. While the carriage assembly 114 is located in the proximal-most position (in relation to the housing 112 of the handle assembly 110), a guidewire can be readily withdrawn from (or inserted into) the rotational atherectomy system 100.

To facilitate positioning of the carriage assembly 114 in the proximal-most position, the clinician operator first actuates the carriage docking latch actuator 118. Then, while the carriage docking latch actuator 118 is actuated, the carriage assembly 114 can be translated to the proximal-most position. In some embodiments, unless the carriage docking latch actuator 118 is actuated the carriage assembly 114 is mechanically prevented from translating to the proximal-most position. In some embodiments, while the carriage assembly 114 is in the proximal-most position, the carriage assembly 114 is releasably latched in the proximal-most position. A second actuation of the carriage docking latch actuator 118 can unlatch the carriage assembly 114 so that it can be translated distally away from the proximal-most position.

In the depicted embodiment, the act of positioning of the carriage assembly 114 in the proximal-most position results in forcing a seal puncture member 124 distally into engagement with the adjustable seal 121. Said another way, the seal puncture member 124 penetrates the self-closing portion of the adjustable seal 121 when the carriage assembly 114 is translated to the proximal-most position. A lumen defined by the seal puncture member 124 becomes aligned with (and in fluid communication with) the lumen defined by the drive shaft 136. Therefore, in that arrangement a passageway is created from the access port 120 defined in the proximal end of the housing 112 to the lumen of the drive shaft 136.

While the carriage assembly 114 is located in the proximal-most position, a guidewire can be readily withdrawn from (or inserted into) the rotational atherectomy system 100. For example, when installing the rotational atherectomy system 100 over a guidewire, the proximal end of the guidewire can first be threaded into the open distal tip of the drive shaft 136. Then the drive shaft assembly 130 (and handle assembly 110) can be pushed distally over the guidewire. Eventually, as the drive shaft assembly 130 (and handle assembly 110) continue to be pushed distally over the guidewire, the proximal end of the guidewire will emerge from the access port 120 defined in the proximal end of the housing 112. That is the case because, while the carriage assembly 114 is located in the proximal-most position, a passageway is opened all the way from the distal tip of the drive shaft 136 to the access port 120 defined in the proximal end of the housing 112. To remove the guidewire from engagement with the rotational atherectomy system 100, while the carriage assembly 114 is located in the proximal-most position the guidewire can be pulled proximally out from the access port 120 defined in the proximal end of the housing 112. After withdrawing the guidewire from the drive shaft 136 (through the adjustable seal 121), the rotational atherectomy system 100 can be operated by supplying compressed gas to the turbine member 119 to drive the rotation of the drive shaft 136.

Figure 9:
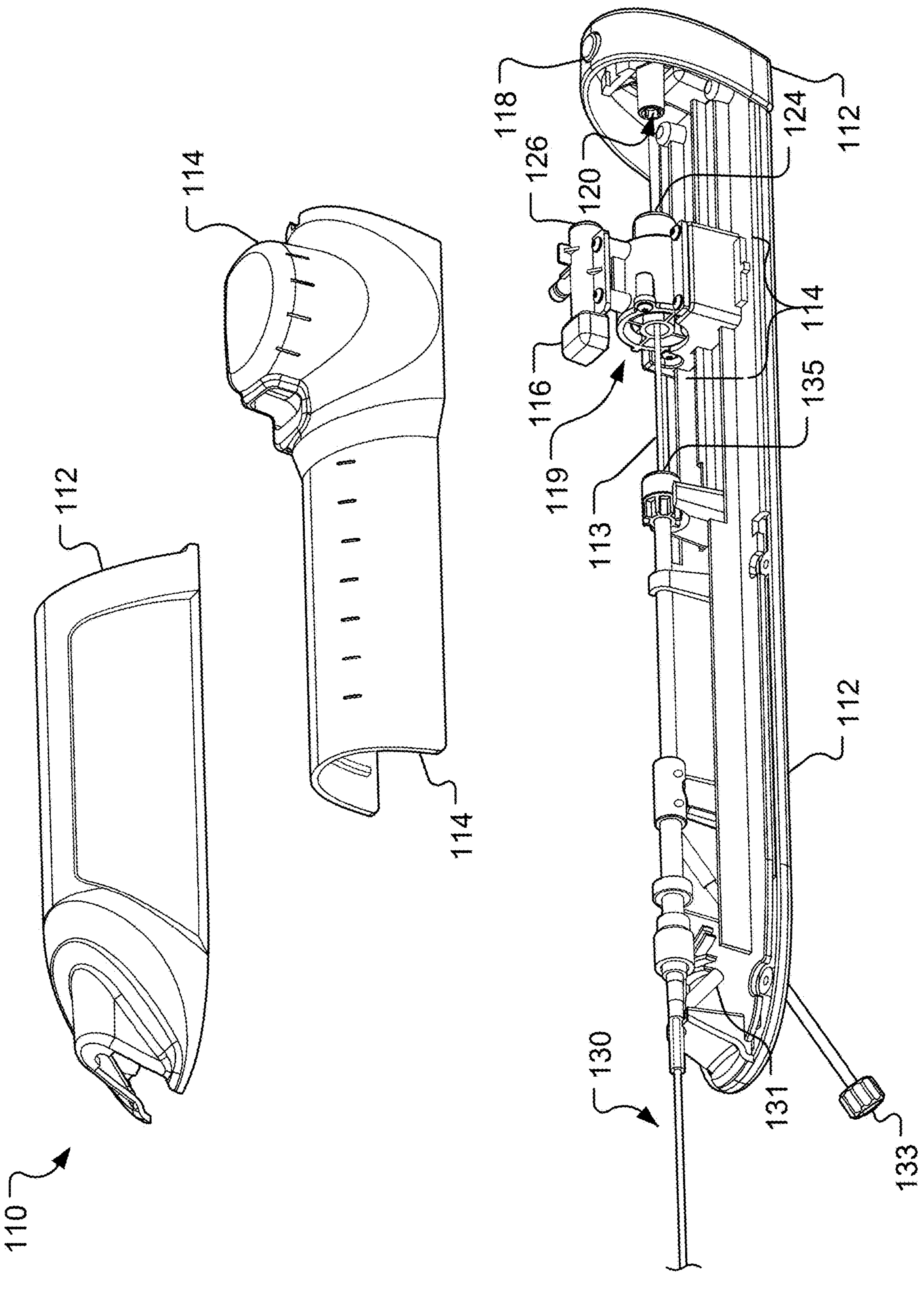
FIG. 9 shows an exploded perspective view of an example handle assembly in accordance with some embodiments.
Figure 10:
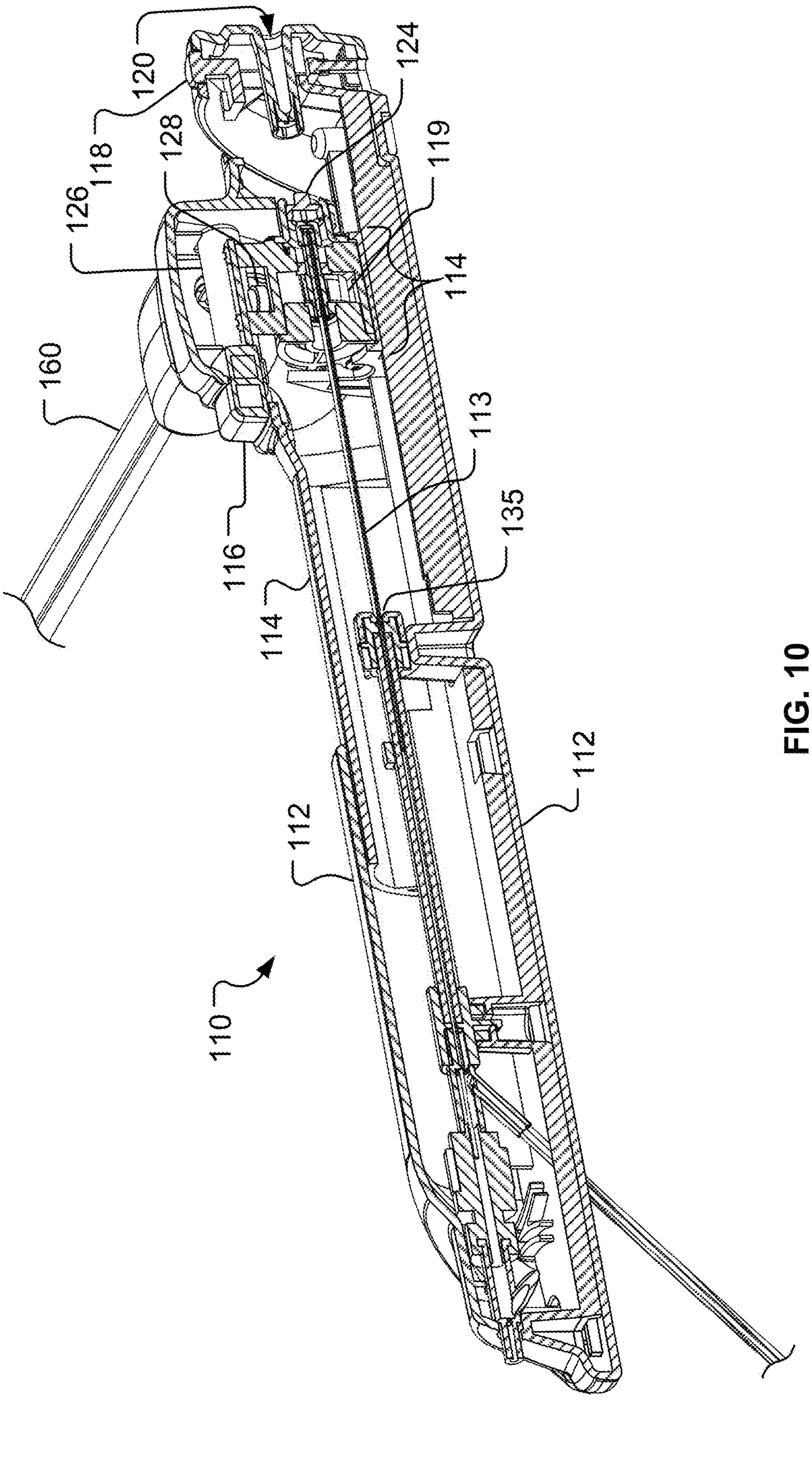
FIG. 10 shows a longitudinal cross-sectional view of the handle assembly of FIG. 9.

Referring to FIGS. 9 and 10, the handle assembly 110 is illustrated in exploded and longitudinal cross-sectional views for additional visibility of the components of the handle assembly 110. The components and functionality of the handle assembly 110 have been described above in reference to FIGS. 1-8.

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:

1. A method of rotational atherectomy comprising:

advancing into a vessel at least one eccentric diamond-coated element fixedly mounted to a distal end portion of a torque-transmitting coil, wherein the torque-transmitting coil is slidably and rotatably disposed within a lumen of a sheath such that said at least one eccentric diamond-coated element is positioned distally of a distal end of the sheath, and wherein the torque-transmitting coil is coupled to a rotational atherectomy control handle configured to control rotation of the torque-transmitting coil, the rotational atherectomy control handle including:

a handle housing having a front housing portion coupled to the sheath and a rear housing portion, the handle housing containing a slidable carriage that is coupled with the torque-transmitting coil, the slidable carriage being slidably translatable in a longitudinal direction relative to both the front housing portion of the handle housing and the sheath so as to longitudinally translate the torque-transmitting coil relative to both the front housing portion of the handle housing and the sheath;

a user interface button configured to activate rotation of the torque-transmitting coil and being mounted with the slidable carriage such that both the user interface button and the slidable carriage are simultaneously translatable in the longitudinal direction while the user interface button is accessible along an upper side of the handle housing;

a carriage lock actuator that is movable relative to the handle housing and is configured to releasably lock the slidable carriage in a locked position relative to the handle housing;

a guidewire access port positioned at the rear housing portion of the handle housing; and a fluid delivery tube connected to the front housing portion of the handle housing at a location distal of the user interface button and proximal of the sheath, wherein the fluid delivery tube is in fluid communication with the lumen of the sheath;

adjusting the carriage lock actuator so that the slidable carriage is unlocked from the locked position relative to the handle housing; and moving the slidable carriage and the user interface button mounted with the slidable carriage relative to the handle housing while the user interface button is in a depressed state to activate rotation of the torque-transmitting coil within the lumen of the sheath.

2. The method of claim 1, controlling the rotation of the torque-transmitting coil according to a speed control setting while the user interface button is in the depressed state.

3. The method of claim 2, wherein a control unit is configured to drive rotation of a rotatable member that is contained in the handle housing and that is coupled with the torque-transmitting coil so that the torque-transmitting coil rotates according to said speed control setting.

4. The method of claim 3, wherein the control unit is positioned external to the handle housing.

5. The method of claim 2, wherein the control unit is configured to drive rotation of the torque-transmitting coil only if a sensor configured to detect a rotation speed of the torque-transmitting coil is in electrical communication with the control unit.

6. The method of claim 2, wherein the control unit is configured to drive rotation of the torque-transmitting coil only if a fluid is delivered through the fluid delivery tube into the lumen of the sheath.

7. The method of claim 1, wherein after said adjusting the carriage lock actuator so that the slidable carriage is unlocked, the slidable carriage is manually translatable during rotation of the torque-transmitting coil so that the at least one eccentric diamond-coated element fixedly mounted to the distal end portion of the torque-transmitting coil is simultaneously movable both in longitudinal translation and in an orbital path.

8. The method of claim 1, wherein the at least one eccentric diamond-coated element fixedly mounted to the distal end portion of the torque-transmitting coil comprises an array of at least three same-shaped eccentric diamond-coated elements.

9. The method of claim 8, further comprising a distal concentric element fixedly mounted to the distal end portion of the torque-transmitting coil at a location that is distally spaced apart from a distal-most eccentric diamond-coated element in the array of at least three same-shaped eccentric diamond-coated elements.

10. The method of claim 9, wherein the distal concentric element comprises a metallic cylindrical element mounted to the torque-transmitting coil and axially aligned with the longitudinal axis of the torque-transmitting coil.

11. The method of claim 10, wherein the metallic cylindrical element has an axial length that is greater than each of the at least three same-shaped eccentric diamond-coated elements.

12. The method of claim 1, wherein a distal extension portion of the torque-transmitting coil extends distally of the at least one eccentric diamond-coated element fixedly mounted to the distal end portion of the torque-transmitting coil.

13. The method of claim 1, further comprising inserting a guidewire through the guidewire access port.

14. The method of claim 1, wherein the at least one eccentric diamond-coated element comprises a metallic burr welded to one or more filars along the distal end portion of the torque-transmitting coil.

15. The method of claim 2, wherein the torque-transmitting coil comprises a coating along at least a portion of an exterior of the torque-transmitting coil.

16. The method of claim 1, wherein the rotational atherectomy control handle further comprises a rotatable member positioned within the handle housing and coupled with the torque-transmitting coil.

17. The method of claim 16, wherein after said adjusting the carriage lock actuator so that the slidable carriage is unlocked, the slidable carriage is configured to longitudinally translate both the torque-transmitting coil and the rotatable member relative to the front housing portion of the handle housing.

18. The method of claim 16, wherein the rotatable member is a turbine member.

19. The method of claim 1, wherein the user interface button is a depressible button along an upwardly extending knob.

20. The method of claim 1, wherein while the depressible button is in the depressed state to activate rotation of the torque-transmitting coil, the torque-transmitting coil rotates at a rotational speed of 20,000 rpm to 160,000 rpm.

* * * * *